United States Patent
Seuret et al.

(10) Patent No.: US 10,352,905 B2
(45) Date of Patent: Jul. 16, 2019

(54) METHOD AND ARRANGEMENT FOR MEASURING THE TIGHTNESS OF A CORE IN AN ELECTRIC MACHINE

(71) Applicant: General Electric Technology GmbH, Baden (CH)

(72) Inventors: Eric Seuret, Baden (CH); Sanjiv Kumar Mishra, Baden (CH); Andrew Lumley, Stafford (GB); Massimiliano Visintin, Baden (CH)

(73) Assignee: General Electric Company, Schenectady, NY (US)

( * ) Notice: Subject to any disclaimer, the term of this patent is extended or adjusted under 35 U.S.C. 154(b) by 61 days.

(21) Appl. No.: 15/352,930

(22) Filed: Nov. 16, 2016

(65) Prior Publication Data
US 2017/0146491 A1    May 25, 2017

(30) Foreign Application Priority Data
Nov. 20, 2015    (EP) .................................... 15195556

(51) Int. Cl.
*G01N 29/07* (2006.01)
*H02K 15/02* (2006.01)
*G01N 29/04* (2006.01)

(52) U.S. Cl.
CPC .......... *G01N 29/07* (2013.01); *G01N 29/045* (2013.01); *H02K 15/02* (2013.01); *G01N 2291/011* (2013.01); *G01N 2291/0231* (2013.01)

(58) Field of Classification Search
CPC ....... G01N 29/07; G01N 29/045; H02K 15/02
See application file for complete search history.

(56) References Cited

U.S. PATENT DOCUMENTS

| 3,943,755 A | 3/1976 | Arii et al. |
| 9,148,045 B2 * | 9/2015 | Visintin ................... G01M 7/00 |

FOREIGN PATENT DOCUMENTS

RU    223587 C2    2/2004

OTHER PUBLICATIONS

European Search Report issued in connection with corresponding EP application No. 15195556.4 dated Jun. 10, 2016.

* cited by examiner

*Primary Examiner* — David Z Huang
(74) *Attorney, Agent, or Firm* — Frank A. Landgraff

(57) ABSTRACT

A method and an arrangement is provided for measuring the tightness of a core composed of laminated sheets used in an electric machine. The method for measuring the tightness of a core of an electric machine composed of sheets, includes supplying a sound wave to the core, measuring the speed of the sound wave in the core, and deducing the tightness of the core from the measured data. The arrangement to measure the tightness of a core of an electric machine composed of sheets, includes a hammering system to pound at the core for generating a sound wave in the core, at least two accelerometers arranged at the core at an axial distance for measuring the speed of the sound wave, and a computer to deduce the tightness of the core from the measured data.

9 Claims, 2 Drawing Sheets

METHOD AND ARRANGEMENT FOR MEASURING THE TIGHTNESS OF A CORE IN AN ELECTRIC MACHINE

TECHNICAL FIELD

The present disclosure relates to a method and an arrangement for measuring the tightness of a core composed of laminated sheets used in an electric machine.

The electric machine is in particular a rotating electric machine such as a synchronous generator to be connected to a gas or steam turbine (turbogenerator) or a synchronous generator to be connected to a hydro turbine (hydro generator) or an asynchronous generator or a synchronous or asynchronous electric motor or also other types of electric machines. The electric machine can also be a motor of different kinds. The requirement to the core of the electric machine in the context of this disclosure is that it is composed of sheets.

BACKGROUND

In an electric machine, the main parts are the rotating rotor and the static stator around the rotor. A key part of the rotor and stator is the core or core package which stator core is composed of stacked and fixed laminated sheets. The highly stressed core is prone to wear which leads to instability over the years of operation. A regular maintenance of the core is necessary thus to assure the stability of the core. The pressure in a stator core is of paramount importance for long and safe machine operations, loose cores generate vibrations leading to stator failures. Several methods and devices are proposed in the state of the art. One method is to arrange a blade or wedge which carries an instrumented tip between the sheets of the core. This method is used to measure the pressure between the core laminations. The reliability of this test method is however in question and only allows the assessment of largely slack cores with highly impaired tightness.

BRIEF DESCRIPTION

It is an object of the subject disclosure to provide a method and a device for measuring the tightness of a core of an electric machine.

This object is achieved with a method and an arrangement as disclosed herein.

In an embodiment, the core is compressed with a defined reference pressure, the speed of the sound wave in the core is measured, then the pressure from the core is released, and the speed of the sound wave in the core without reference pressure is measured. Afterwards, the ratio between the speed of the sound wave with and without reference pressure is calculated. With these measures the quality of measurement can be improved as several parameters impairing the measurement are suppressed.

In an example of the subject disclosure the reference pressure is applied to the core by a plier system. Such a plier system is suitable to exert a specific pressure to the core in the axial direction. The plier system comprises a hydraulic device and arms to reach between the sheets of the core. For example, the arms reach into ventilation ducts of the core.

In a further example of the subject disclosure the sound wave is generated by a hammering system. The hammering system comprises a massive hammer to impose a shock or strike to the core. The strike is done perpendicular to the longitudinal axis of the core but may also be executed in an axial direction of the core. The hammering system is steered and coordinated with the measurement.

In a further example of the subject disclosure the speed of the sound wave in the core is measured by two accelerometers arranged at different positions with a known distance to each other along the axis of the core. The accelerometers are triggered when the vibrations at the core excel a specific value. The time between triggering the two accelerometers is measured and from the known distance the speed of the sound wave is calculated.

BRIEF DESCRIPTION OF THE DRAWINGS

Further characteristics and advantages will be more apparent from the description of a non-exclusive embodiment of the arrangement and method, illustrated by way of non-limiting example in the accompanying drawings, in which.

DETAILED DESCRIPTION OF EXEMPLARY EMBODIMENTS

Figure 1:
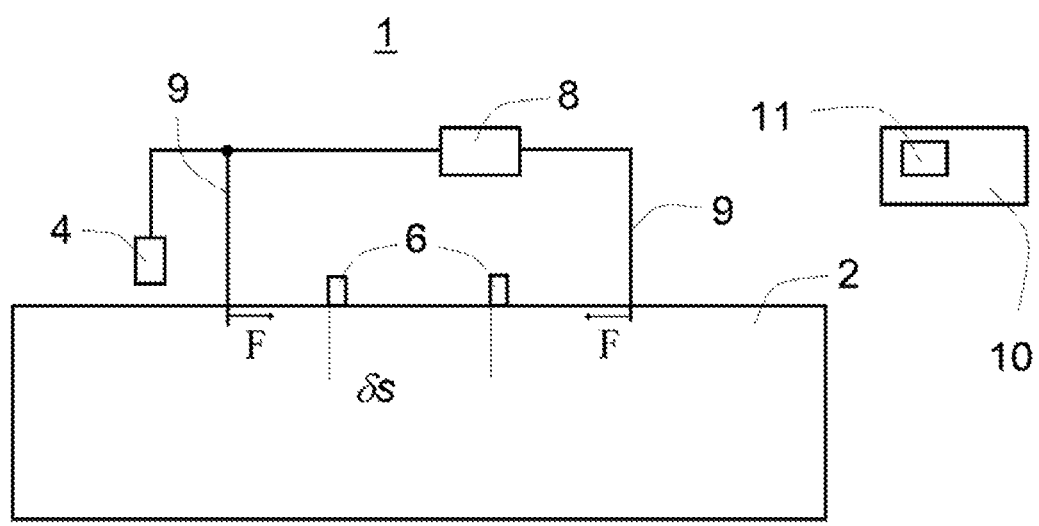
FIG. 1 shows a schematic block diagram of an arrangement according to an example of the subject disclosure with a stator core, a hammering system to pound at the core and produce a sound wave in the core, two accelerometers arranged at the core to measure the sound speed, a plier system to generate a reference pressure in the core via two arms, and a computer to receive and calculate the measured data.

With reference to FIG. 1, this shows a schematic block diagram of an arrangement to measure the tightness of a core according to an example of the subject disclosure.

FIG. 1 shows a schematic block diagram of an arrangement 1 according to an example of the subject disclosure. Shown is a stator core 2 of an electric machine in a schematic side view which length is in the range of several metres for big machines as turbogenerators. At the left above and adjacent to the core 2 a hammering system 4 is shown. The hammering system 4 comprises a massive hammer to pound at the core 2, in FIG. 1 from above. The hammer of the hammering system 4 is activated by a signal from a dedicated computer 10. This activation signal can be transferred via signal lines or wirelessly. The strike of the hammer on the surface of the core 2 produces a sound wave which propagates in the material of the core 2. Two accelerometers 6 are arranged at the core 2 which measure an acceleration or vibration caused by the strike of the hammering system 4. The acceleration data is transferred to the computer 10 via signal lines or wirelessly. As one accelerometer 6 is more distant to the hammering system 4 than the other the sound wave reaches the more distant accelerometer 6 later. The time span between the signals from the both accelerometers 6 is calculated and translated in the computer 10 to the speed of the sound with the known distance δs of the accelerometers 6 to each other. The result of the speed of the corresponding measurement is shown at a display 11 at the computer 10. It was found that the sound speed is a measure for the tightness of the core 2. Through investigations it was discovered that a sound wave increases speed when the axial pressure in the core 2 increases. On basis of this knowledge the pressure in the core 2 or tightness of the core 2 is deduced from the measured data in the computer 10. This data is transferred to the computer 10 and depicted on the display 11. The operator of the system or arrangement 1 can decide with the help of the measurement results whether the core 2 can continue operation or needs a repair. Alternatively, the software on the computer 10 provides conclusions on basis of the measurement results to support the decision making of the operator. In each case the measurement of the sound wave provides a useful indication to the operator regarding the operability of the core 2. The measurement is repeated with different positions of the accelerometers 6 at the core 2 to investigate different areas at the core 2. By this means deficiencies regarding the tightness of the core 2 are located precisely.

Above, one example of the subject disclosure without applying a pressure to the core 2 is described. In a further development, a reference pressure is generated by a plier system 8. The plier system 8 comprises a hydraulic system to create a substantial pressure to the core 2. This pressure is exerted to the core 2 via two arms 9 at the plier system 8 which reach into gaps of the core 2. The gaps can be ventilation ducts of the core 2. The arms 9 have an axial distance from each other and span the area of the core 2 which is of interest, at least the area in which the accelerometers 6 are arranged at the core 2. The force F or pressure is directed inwardly as indicated by the arrows in FIG. 1, this means the pressure on the sheets of the core 2 is enhanced by the plier system 8 in a controlled manner. The pressure exerted on the core 2 is defined by the plier system 8 and referred to as reference pressure. This reference pressure is for example 1 MPa. In this second example first a measurement is executed as described under the example above, the measurement data is transferred and stored in the computer 10. Second, the reference pressure is applied as described and the measurement of the sound wave is conducted in a similar way. The two measurement results are then further calculated, the ratio between the sound speed without a reference pressure and the sound speed with applied reference pressure is calculated in the computer 10. The resulting quotient gives an even better understanding of the tightness of the core 2. This is due to the finding that parameters influencing the sound wave speed, like the material, age, or grain orientation, are suppressed. Those parameters being multiple and variable. Calculating the ratio of the measured sound speeds according to this example excludes these influencing quantities. Both examples provide results on which basis a planning of maintenance and repair is done in the contrary to the state of the art. The sound wave measurement allows for a precise determination of the tightness of the core 2. In the state of the art merely the conclusion is delivered whether to replace defect parts or not. Embodiments of the subject disclosure however makes feasible to predict a residual operation time of the core 2 deduced from the measurement results. From the residual pressure in specific parts of the core 2 a residual operation time of this part of the core 2 is deduced by the operator or by the software on the computer 10.

Figure 2:
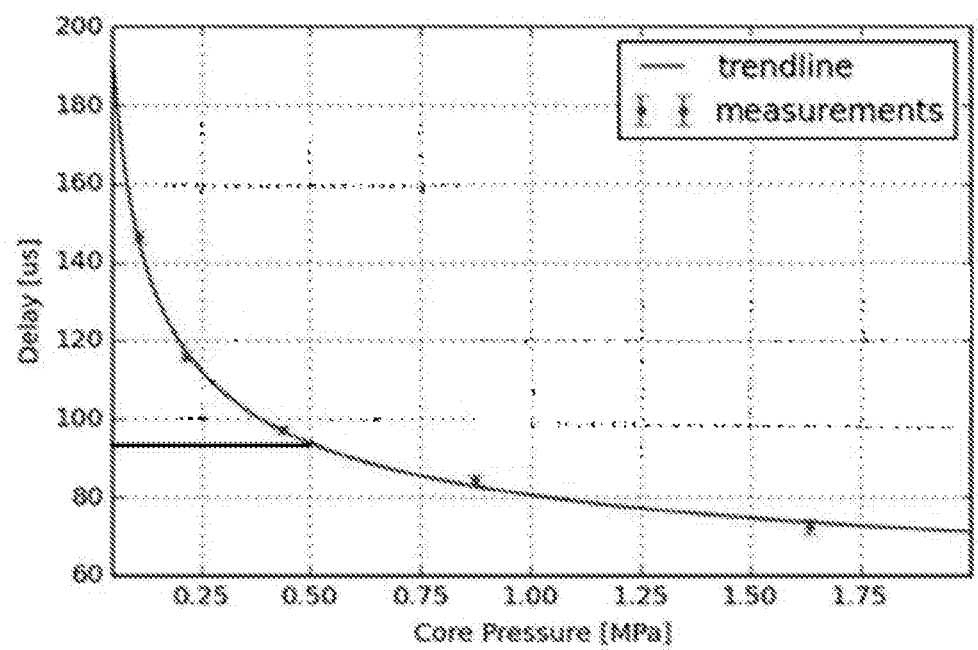
FIG. 2 shows an exemplary curve of measured time delays in µs in dependency of different reference pressures applied to the core in MPa.

FIG. 2 shows an exemplary curve according to the second example of the subject disclosure. At the horizontal axis the reference pressure applied to the core 2 is plotted in MPa. At the vertical axis the measured time delay of the sound wave between the two points defined by the distant accelerometers 6 in μs is plotted. It can be seen that the curve is strongly changing with the reference pressure. At zero reference pressure a time delay of approximately 190 μs is measured, with an applied reference pressure of 1 MPa a time delay of approximately 80 μs is measured, the sound wave has doubled speed. According to the second example described above the quotient of these two measurement results is calculated in the computer 10. The sound wave speed with applied pressure is used as a reference value. From this quotient the tightness of the core 2 is deduced by tables stored in the computer 10. The measurements of the speed of the sound wave can be repeated with any other pressure applied to the core 2. In FIG. 2 five measurements are done with five different core pressures illustrated by five points at the curve. Accordingly, five delay times are measured by the accelerometers 6. In any case the tightness of the core 2 is measured at different positions along the core 2 to obtain a distribution of residual pressure of the sheets along the core 2. This distribution serves for analysing all parts of the core 2 in terms of immediate need for maintenance or prediction of a residual operation time of the individual core parts.

While the subject disclosure has been described in detail with reference to exemplary embodiments thereof, it will be apparent to one skilled in the art that various changes can be made, and equivalents employed, without departing from the scope of the subject disclosure. The foregoing description of the embodiments of the subject disclosure has been presented for purposes of illustration and description. It is not intended to be exhaustive or to limit the subject disclosure to the precise form disclosed, and modifications and variations are possible in light of the above teachings or may be acquired from practice of the subject disclosure. The embodiments were chosen and described in order to explain the principles of the subject disclosure and its practical application to enable one skilled in the art to utilize the subject disclosure in various embodiments as are suited to the particular use contemplated. It is intended that the scope of the subject disclosure be defined by the claims appended hereto, and their equivalents.

What is claimed is:

1. A method for measuring the tightness of a core of an electric machine comprised of sheets, comprising the steps of:
   compressing the core with a reference pressure;
   measuring a speed of a sound wave in the core with the reference pressure by supplying a first sound wave to the core;
   releasing the reference pressure from the core;
   supplying a second sound wave to the core;
   measuring the speed of the sound wave in the core without the reference pressure applied to the core;
   calculating a ratio between the speed of the sound wave with and without the reference pressure; and
   deducing the tightness of the core from the ratio.

2. The method according to claim 1, wherein the reference pressure is applied to the core by a plier system.

3. The method according to claim 1, wherein the sound wave is generated by a hammering system.

4. The method according to claim 1, wherein the speed of the sound wave in the core is measured by two accelerometers arranged at different positions along an axis of the core.

5. The method according to claim 1, wherein the reference pressure is 1 MPa.

6. The method according to claim 1, wherein five different reference pressures are used to compress the core and five measurements of a speed of a sound wave in the core are obtained.

7. An arrangement to measure the tightness of a core of an electric machine comprised of sheets, comprising:
   a plier system configured to apply a reference pressure to at least a part of the core;
   a hammering system configured to pound at the core for generating a sound wave in the core;

at least two accelerometers arranged at the core at an axial distance for measuring a speed of the sound wave, and a computer configured to deduce the tightness of the core by calculating a ratio between the speed of the sound wave with and without the reference pressure applied to the core.

8. The arrangement according to claim 7, wherein the reference pressure is 1 MPa.

9. The method according to claim 7, wherein five different reference pressures are used to compress the core and five measurements of a speed of a sound wave in the core are obtained.

* * * * *